(12) United States Patent
Loccufier et al.

(10) Patent No.: US 6,361,920 B1
(45) Date of Patent: Mar. 26, 2002

(54) PHOTOGRAPHIC MATERIAL CONTAINING A NOVEL HYDRAZIDE TYPE

(75) Inventors: Johan August Loccufier, Zwijnaarde; Stefaan Lingier, Assenede; Pascal Frans Meeus, Turnhout, all of (BE)

(73) Assignee: AGFA Gevaert (BE)

( * ) Notice: Subject to any disclaimer, the term of this patent is extended or adjusted under 35 U.S.C. 154(b) by 0 days.

(21) Appl. No.: 09/661,245

(22) Filed: Sep. 13, 2000

Related U.S. Application Data
(60) Provisional application No. 60/155,333, filed on Sep. 22, 1999.

(30) Foreign Application Priority Data

Sep. 15, 1999 (EP) .............................................. 99203011

(51) Int. Cl.[7] .................................................. G03C 1/06
(52) U.S. Cl. ........................ 430/264; 430/598; 430/607
(58) Field of Search ................................ 430/264, 598, 430/607

(56) References Cited

U.S. PATENT DOCUMENTS

| | | | | |
|---|---|---|---|---|
| 5,558,974 A | * | 9/1996 | Loccufier et al. | 430/264 |
| 5,989,774 A | * | 11/1999 | Loccufier et al. | 430/264 |
| 5,998,087 A | * | 12/1999 | Loccufier et al. | 430/264 |

FOREIGN PATENT DOCUMENTS

| | | |
|---|---|---|
| EP | 0444506 | 2/1991 |
| EP | 0816913 | 6/1997 |
| EP | 0902319 | 10/1997 |
| JP | 06175253 | 6/1994 |

* cited by examiner

*Primary Examiner*—Geraldine Letscher
(74) *Attorney, Agent, or Firm*—Joseph T. Guy; Nexsen Pruet Jacobs & Pollard LLC

(57) ABSTRACT

A high contrast silver halide photographic material is disclosed containing a new type of hydrazide compound represented by following general formula I, the different symbols of which are defined in the description.

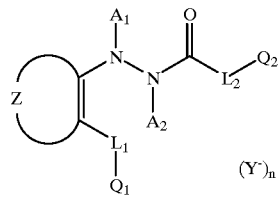

formula I

The photographic material is preferably a graphic arts material for pre-press applications. High gradation and excellent dot quality, exposure latitude and stability on continuous processing are obtained.

5 Claims, No Drawings

PHOTOGRAPHIC MATERIAL CONTAINING A NOVEL HYDRAZIDE TYPE

This application claims benefit of Provisional Applications No. 60/155,333 filed Sep. 22, 1999.

FIELD OF THE INVENTION

The present invention relates to high contrast photographic materials with improved properties and to a novel class of nucleating agents contained in them.

BACKGROUND OF THE INVENTION

In graphic arts reproduction processes the original image appearing to have a continuous tone gradation is reproduced by a collection of a large number of dots and/or lines, either by optical means in the case of a camera film, or by electronic means in case of a recorder film. The tone of the reproduced image is influenced by both the size of the dots and lines and their density. A graphic arts film exposed in a way to exactly render the relative proportions of black and white in the original must produce dots and lines of sufficient density; another reason herefore is the fact that no substantial amount of copying light may be transmitted through the dots and lines in a further duplicating cycle or during the direct exposure of a printing plate. Therefore a photographic element showing high contrast or so-called "lith gradation" on development is highly desired. Furthermore the generated or reproduced dots and lines must exhibit a well-shaped form and sharp edges.

This most desired combination of high contrast and excellent dot quality is commonly termed "lith quality". The goal of achieving optimal lith quality is reached by the combination of specially designed graphic arts material and appropriate processing systems. A first group of such processing systems consists of the traditional "lith developers" characterized by the presence of hydroquinone as the sole developing agent and a low but critical sulphite ions content giving rise to an infectious development mechanism, as was described by Yule in *The Journal of the Franklin Institute,* Vol. 239, p. 221–223, (1945). This type of development is believed to proceed autocatalytically. The low concentration of sulphite is maintained by the progressive dissociation of an aldehyde-bisulphite adduct. However these conventional lith developers are rather instable in time and require complicated replenishment systems for both oxidation and exhaustion. Furthermore their developing capacity is limited due to the fact that they contain hydroquinone as the sole developing agent.

In more recent times so-called "hard dot Rapid Access" developers were introduced on the market which combine a good stability with a "lith quality" in the reproduction of lines and screen dots. Examples of such developers and corresponding appropriate photographic materials include the GRANDEX system, marketed by FUJI PHOTO ltd., AGFASTAR, marketed by AGFA-GEVAERT N.V. and the ULTRATEC system, marketed by EASTMAN KODAK Co. Some of these systems make use of the contrast promoting action, induced by a nucleating mechanism, of hydrazine derivatives known for long time in the photographic art. As described by Simson et al., U.S. Pat. No. 4,650,746, use of a hydrazine compound permits the use of an auxiliary development agent in combination with the hydroquinone type of developing agent so that the development capacity can be increased. It also permits the presence of a relatively high sulphite concentration in order to protect the developer against aerial oxidation and thereby prolonging its effective working life. Further early disclosures on hydrazine compounds, incorporated either in a photographic element or in a developing solution, include Smith U.S. Pat. No. 2,410,690, Stauffer U.S. Pat. No. 2,419,974, Trivelli U.S. Pat. No. 2,419,975 and Hunsberger U.S. Pat. No. 2,892,715 and an article by Stauffer, Smith and Trivelli entitled "The influence of photographic developers containing hydrazine upon the characteristic curves of photographic materials", *The Journal of the Franklin Institute,* Vol. 238, p. 291–298, Oct. 1944. Since then the photographic world has undertaken extensive research on hydrazine chemistry for use in photographic applications and the recent patent literature on new hydrazine derivatives and on the combination of known or new hydrazines with other useful ingredients in photographic elements or developers is abundant.

A practical early recognized problem was caused by the high pH levels needed for the developers containing hydrazine compounds or used with photographic elements containing these compounds in order to get the maximum effect on contrast. The teaching of Nothnagle U.S. Pat. No. 4,269,929 brought a solution to this problem. Here a method for high contrast development was disclosed involving a hydrazine compound, either in the photographic element or in the developer, said developer further containing a hydroquinone developing agent, a 3-pyrazolidinone developing agent, sulphite ions, and a "contrast-promoting amount" of an amino compound. In a preferred embodiment the hydrazine compound was incorporated in the photographic material. According to this patent, issued May 26, 1981, this particular combination of ingredients allow the use of a rather moderate alkaline pH for the developing solution while retaining the desired high contrast and dot quality characteristics. In this way an excellent combination of lith quality of the finished material, high developing capacity and long effective life of the developer was achieved.

Since then intense research has been conducted to improve the performance of hydrazines, mostly acylhydrazides, and in particular to make them workable in combination with conventional rapid access developers having a pH around 10.5 and containing no special ingredients such as amine boosters. Specific new hydrazide derivatives are described, e.g. in JP-A 57-99635, EP 0 217 310, JP-A 61-270744, JP-A 62-89958, EP 0 283 040, EP 0 301 799, U.S. Pat. Nos. 4,816,373, 4,847,180, JP-A 63-294552, JP-A 63-44649, JP-A 63-8715, EP 0 283 040, JP-A 01-100530, EP 0 345 025, JP-A 01-201650, EP 0 356 898, DE 38 29 078, U.S. Pat. Nos. 4,950,578, 5,028,510, EP 0 399 460, U.S. Pat. No. 5,006,445, JP-A 01-285940, U.S. Pat. Nos. 4,988,604, 4,994,365, JP-A 02-300474, JP-A 02-302750, JP-A 02-841, JP-A 02-947, EP 0 444 506, EP 0 479 156, JP-A 04-283743, EP 0 539 925, U.S. Pat. No. 5,212,045, EP 0 569 983, U.S. Pat. Nos. 5,284,732, 5,447,820, 5,424,170, EP 0 671 654, WO 95/32452, WO 95/32453, DE 19522725, EP 0 713 130, U.S. Pat. No. 5,451,486, EP 0 731 385, EP 0 736 798, EP 0 763 771, EP 0 782 041, EP 0 782 042, U.S. Pat. Nos. 5,686,222, 5,858,610, 5,702,866, and GB 2 297 747.

A study on the nucleating mechanism of acylhydrazides, responsible for infectious development, can be find in Simson, SPSE, 25th Fall Symposium, (1985), p. 48. Other studies include Kitchin et al., *J. Phot. Sci.,* Vol. 35, (1987), p. 162, Shinoara et al., *J. Photogr. Sci.,* Vol. 35, (1987), p. 181, Kobayashi, *J. Phot. Sci.,* Vol. 43, (1995), p. 186, and Yamada, *J. Imag. Sci. Techn.,* Vol. 43, No. 1, (1999), p. 103.

An important technological breakthrough was the development and use of sulphonamido-arylhydrazides as disclosed in EP 0 286 840 and U.S. Pat. No. 5,104,769, which proved to be a very reactive and effective type. Another main progress was the use of hydrazides, especially sulphonamido-arylhydrazides in combination with so-called "incorporated boosters", such as disclosed in Machonkin U.S. Pat. No. 4,975,354, which can be incorporated into the photographic material itself instead of the developer. Still other graphic arts systems are based on the use of hydrazine types that can release a photographically useful group, e.g. an accelerator or a development restrainer, such as disclosed in e.g. EP 0 393 720, EP 0 393 721, EP 0 399 460, U.S. Pat. No. 5,258,259, EP 0 420 005, U.S. Pat. Nos. 5,252,438 and 5,262,274.

In EP 0 816 913 a new class of active arylhydrazides is disclosed having in ortho position a substituent comprising a pyridinium, quinolinium or isoquinolinium group. With this class of hydrazides high gradation was obtained. According to a further improvement on this class of compounds disclosed in EP 0 902 319 the pyridinium, quinolinium or isoquinolinium group is substituted by an aliphatic chain comprising at least one carbon-carbon triple bond.

The present invention extends the teachings on hydrazine compounds in photographic silver halide materials, and constitutes a further improvement to the teachings of EP 0 816 913 and EP 0 902 319 cited above.

OBJECTS OF THE INVENTION

It is the object of the present invention to provide a new class of active hydrazide nucleating agents for use in high contrast photographic materials.

It is a further object of the present invention to provide photographic materials for graphic arts applications with improved gradation, image quality and exposure latitude.

It is still a further object of the present invention to provide a photographic material with improved stability on long-run continuous processing.

SUMMARY OF THE INVENTION

The objects of the present invention are realized by providing a photographic material comprising a support, at least one emulsion layer, and optionally one or more other hydrophilic layers, characterized in that said emulsion layer or another hydrophilic layer adjacent to said emulsion layer contains a compound according to following general formula I:

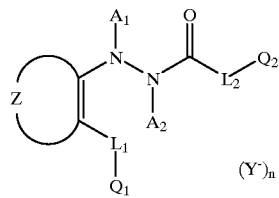

formula I wherein:
1) $L_1$ is a divalent linking group consisting of a linear chain having at most two atoms in said linear chain,
2) $Q_1$ is a cationic nitrogen containing aromatic heterocyclic ring,
3) $L_2$ is a divalent linking group, selected from the group consisting of a substituted or unsubstituted alkylene group, a substituted or unsubstituted alkylene group having a heteroatom in its chain, a substituted or unsubstituted arylene group, a substituted or unsubstituted heteroarylene group, and —CO—N(R)—$L_3$—, wherein R represents hydrogen, a substituted or unsubstituted alkyl group, a substituted or unsubstituted aryl group, or a substituted or unsubstituted heteroaryl group, and $L_3$ represents a substituted or unsubstituted alkylene group, a substituted or unsubstituted arylene group, or a substituted or unsubstituted heteroarylene group, 4) $Q_2$ is a cationic group preferably selected from ammonium, sulfonium or phosphonium), 5) Z represents the necessary atoms to form an aromatic or heteroaromatic ring, 6) each of $A_1$ and $A_2$ independently represents a hydrogen, a group capable of yielding a hydrogen under alkaline photographic processing conditions or a $SO_2R$ group, provided that, if $A_1$ is $SO_2R$, $A_2$ is a hydrogen and vice versa. R represents an alkyl or aryl group, 7) $Y^-$ is a negatively charged counterion to compensate the positive charge of the cationic functional groups.

DETAILED DESCRIPTION OF THE INVENTION

A comparison compound used in the examples furtheron is following compound I:

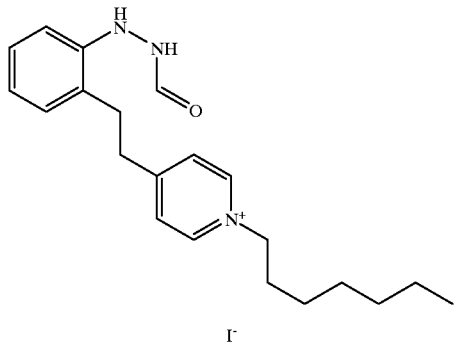

Typical invention compounds according to general formula I are given below:

compound II:

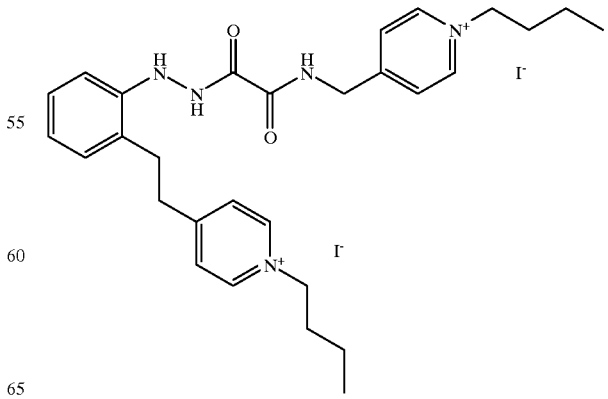

compound III:
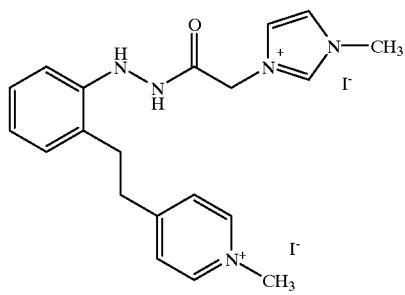
compound IV:
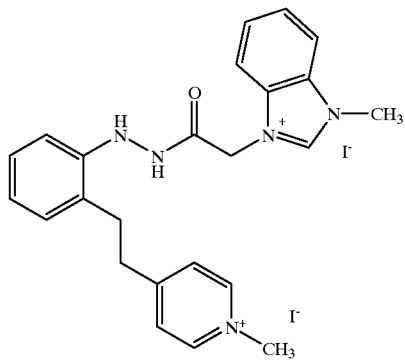
compound V:
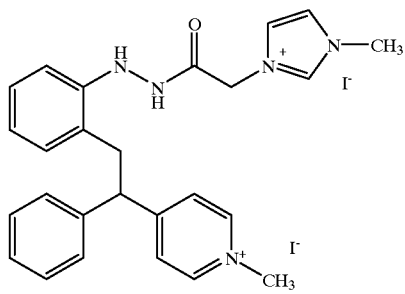
compound VI:
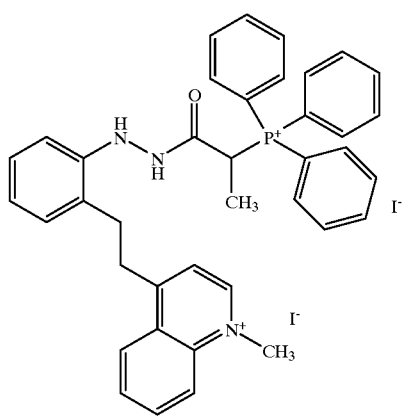
compound VII:
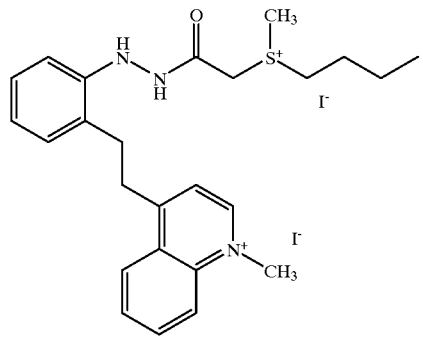
compound VIII:
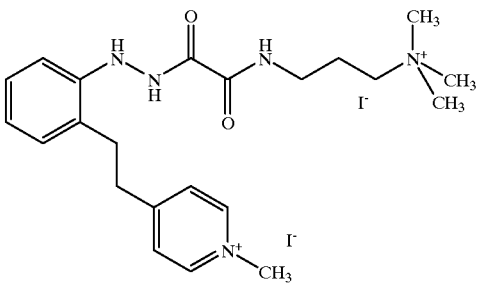
compound IX:
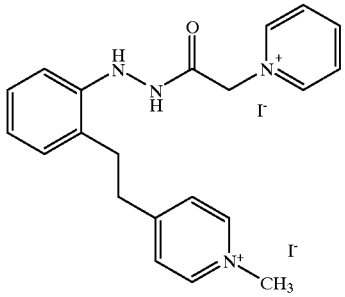
compound X:
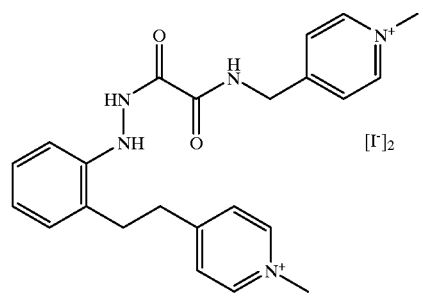
Synthesis of the Invention Compounds
I. The Oxalyl-amide Hydrazides
I.1 The Synthesis of Intermediates
In general the oxalyl-ester intermediate is prepared according to scheme I:

Scheme I

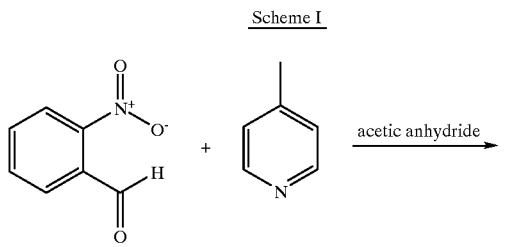

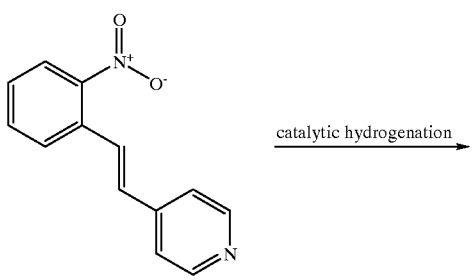

R = H    (1)

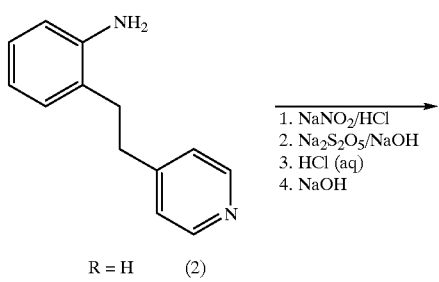

R = H    (2)

1. NaNO₂/HCl
2. Na₂S₂O₅/NaOH
3. HCl (aq)
4. NaOH

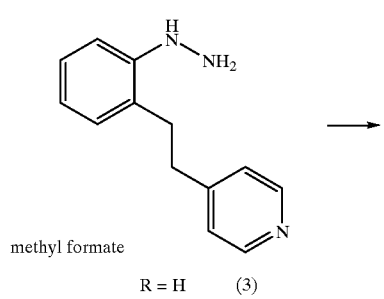

R = H    (3)

methyl formate

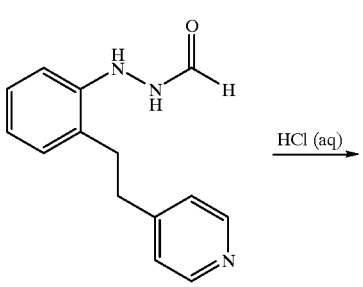

Intermediate A

HCl (aq)

-continued diethyl oxalte (4) •2HCl

Intermediate B

Condensation of the 4-methyl-pyridine and 2-nitrobenzaldehyde (1)

0.4 mol of 4-methyl-pyridine and 0.4 mol of 2-nitrobenzaldehyde were added to 56 ml of acetic anhydride. The mixture was refluxed for 4 hours. The mixture was allowed to cool down and the reaction product was isolated by neutralizing the formed acetic acid with a 10 N NaOH solution. The precipitated product was washed with ethanol.

Catalytic Hydrogenation (2)

22.4 g of the nitro-compound was dissolved in 138 ml of methanol. 0.23 g 5% Pd on C was added and the hydrogenation was carried out at 35° C. using 50 bar hydrogen pressure. The mixture was allowed to cool down to room temperature and the catalyst was removed by filtration. The mixture was concentrated to one third of its volume and the product was precipitated by adding 20 ml water.

The Synthesis of the Intermediate Hydrazine (3)

0.25 mol of the aniline was added to 125 ml of water. 83.5 ml of a concentrated HCl-solution was added and the mixture was cooled to 0° C. 0.26 mol of NaNO₂ in 50 ml of water was added while the temperature was kept below 5° C. The reaction was allowed to continue for an additional 30 minutes at 0° C.

While the diazotation was going on, a solution of 104.5 g of $Na_2S_2O_5$, 220 ml 5 N NaOH and 200 ml water was prepared and heated to 75° C.

The diazonium-solution was added to the solution of sulfite, generated fro the reaction of metabisulfate and sodium hydroxide, during 35 minutes. After 2 hours at 75°

C., two extra portions of $Na_2S_2O_5$/NaOH were added and the reaction was allowed to continue for an extra two hours.

The reaction mixture was cooled to 25° C. and 280 ml of concentrated HCl was added. The mixture was heated to 95° C. and the hydrolysis was allowed to continue for 4 hours. After cooling down to room temperature, the reaction mixture was neutralized with 10 N NaOH. The hydrazine precipitated from the medium as a grey brown amorphous solid. The crude hydrazine was used without further purification.

Intermediate A 30 g of the crude hydrazine was dissolved in 89 ml of methyl formate and refluxed for four hours. The formyl hydrazide precipitated from the medium. The product was isolated by filtration and washed with methyl formate.

Hydrolysis of Intermediate A (4)

24 g of the formylhydrazide was dissolved in 50 ml of concentrated HCl. The reaction mixture was heated to 75° C. and the hydrolysis was allowed to continue for 30 minutes. On cooling, the bis-chlorohydrate of the hydrazine precipitated from the medium. The product was isolated by filtration, washed with 75 ml of ethanol, followed by 75 ml of t.-butyl methyl ether and dried.

Intermediate B 11.2 ml of triethyl amine was added slowly to a suspension of 11.4 g of the hydrazine bis-chlorohydrate in 10 ml of ethanol and 44 g of diethyl oxalate. The temperature increased to 45° C. The mixture was heated to 80° C. for 1 hour. The reaction mixture was allowed to cool down to room temperature. 50 ml of hexane was added. The crude product was isolated by filtration, treated with 50 ml water, followed by 100 ml of ethyl acetate/t.-butyl methyl ether 1/1.

I.2 The Synthesis of Compound II

Compound II was prepared according to scheme II, starting from intermediate B.

Scheme II

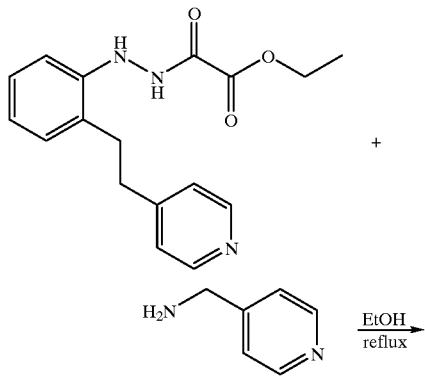

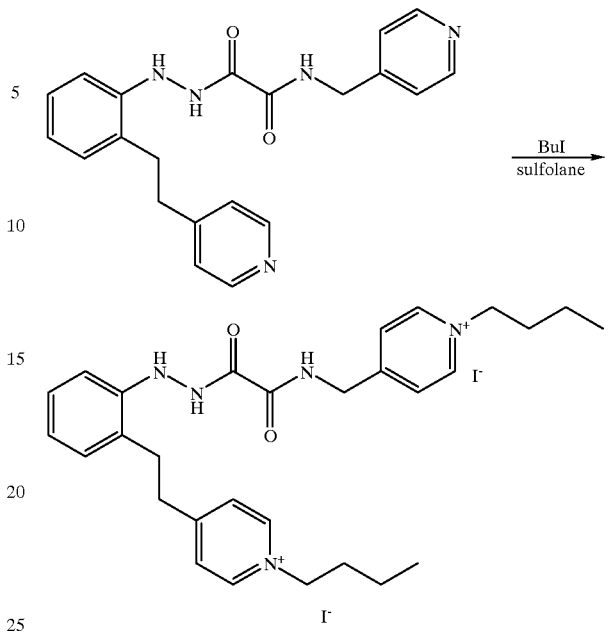

The Aminolysis of the Oxalate Ester 50 mmol of the oxalate ester was added to 200 ml of ethanol. 60 mmol of 4-aminomethyl pyridine was added and the reactionmixture was refluxed for 6 hours. After cooling down to room temperature, the product was isolated by filtration, washed with ethanol and dried.

The Quaternization 20 mmol of the intermediate oxalyl amide hydrazide was added to 50 ml of sulfolane. 60 mmol of butyl iodide was added and the mixture was heated to 105° C. for 30 minutes. The reaction mixture was allowed to cool down to room temperature and pourred into 400 ml of ethyl acetate. The product precipitated as an oil. The solvent was decanted and 400 ml ethyl acetate was added. The product crystallized slowly and was isolated by filtration. The product was treated again with 500 ml of ethyl acetate, isolated by filtration and dried.

II. The Synthesis of Compound III

Compound III was prepared according to scheme III.

Scheme III

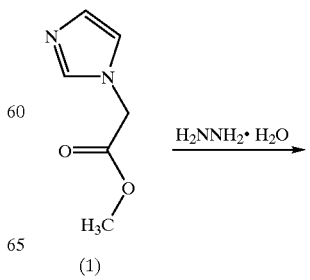

(1)

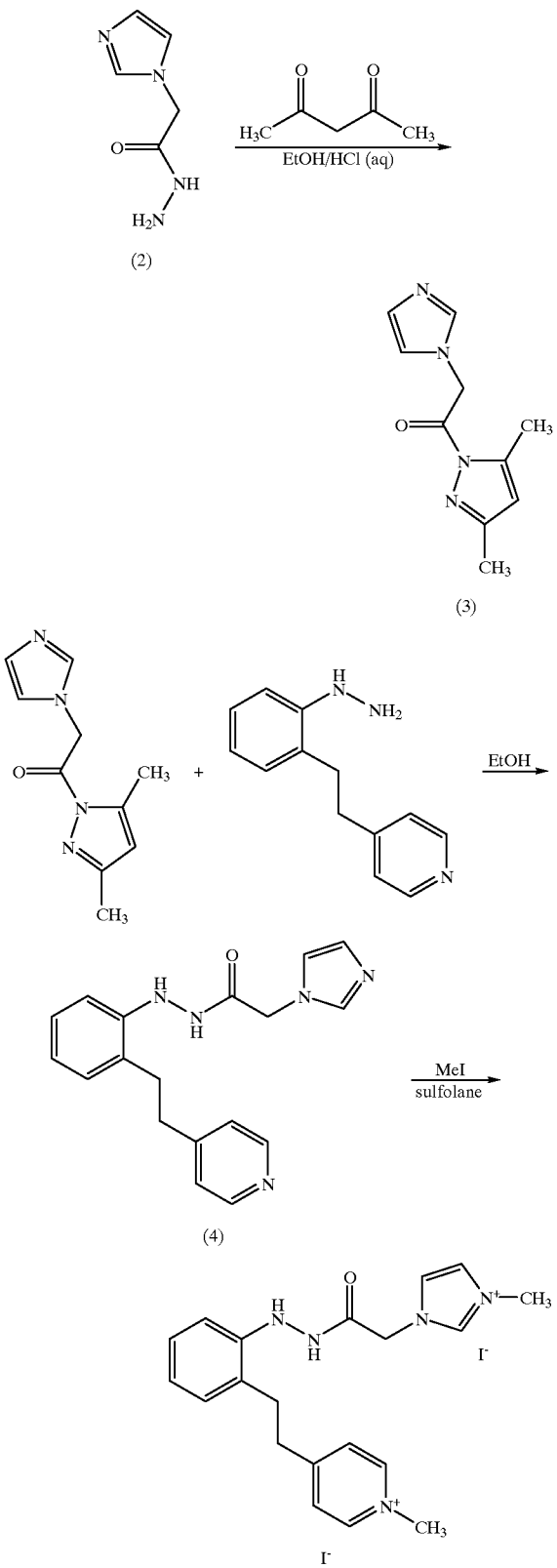

0.6 mol hydrazine hydrate was added and the mixture was refluxed for two and a half hours. After cooling down to room temperature, the reaction mixture was evaporated to a quarter of its volume. On standing, compound (2) crystallized from the medium. 100 ml of ethylacetate was added and the product was isolated by filtration. The compound was treated twice with 100 ml of ethyl acetate/acetonitrile 1/1 and dried.

The Synthesis of Compound (3)

0.11 mol of compound (2) was added to 100 ml of ethanol. 22 ml of HCl 5N was added. 0.12 mol of acetyl acetone in 10 ml of ethanol was added. The reaction was allowed to continue for 1 hour at 35° C. The solvent was removed under reduced pressure. The residue was treated with 100 ml of methylenechloride and 100 ml of water. The aqueous layer was neutralized with triethyl amine. The neutralized aqueous layer was extracted a second time with 100 ml of methylene chloride. The pooled methylene chloride fractions were dried over $MgSO_4$. The organic solvent was removed under reduced pressure and compound (3) was isolated as a viscous oil.

The Synthesis of Compound (4)

42 mmol of the hydrazine (prepared as described above) was dissolved in 50 ml of ethanol. 44 mmol of compound (3) was added and the reaction was allowed to continue for 12 hours at room temperature. The solvent was removed under reduced pressure and the residue was treated four times with 250 ml of ethyl acetate. Compound (4) crystallized finally with some difficulty and was isolated by filtration. Due to the limited storage stability, the compound was used immediately for quaternization.

The Synthesis of Compound III 15.5 mmol of compound (4) was dissolved in 30 ml of sulfolane. 46.5 mmol of methyl iodide was added and the reaction was allowed to continue for 2 hours at 40° C. The reaction mixture was pourred into 40 ml of toluene. The solvent was decanted and the oily residue was treated again with 40 ml of toluene. This was repeated with 100 ml of isopropyl acetate, 100 ml of ethyl acetate and 60 ml of ethyl acetate. Compound III finally crystallized and was isolated by filtration.

III. The Synthesis of Compound IV

Compound IV was prepared according to scheme IV.

Scheme IV

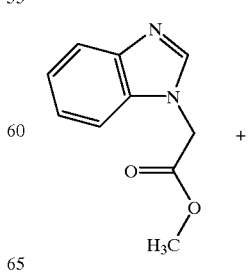

(1)

The Synthesis of Compound (2)

0.2 mol of compound (1) (from imidazole and chloro acetic acid methyl ester) was dissolved in 150 ml of ethanol.

-continued

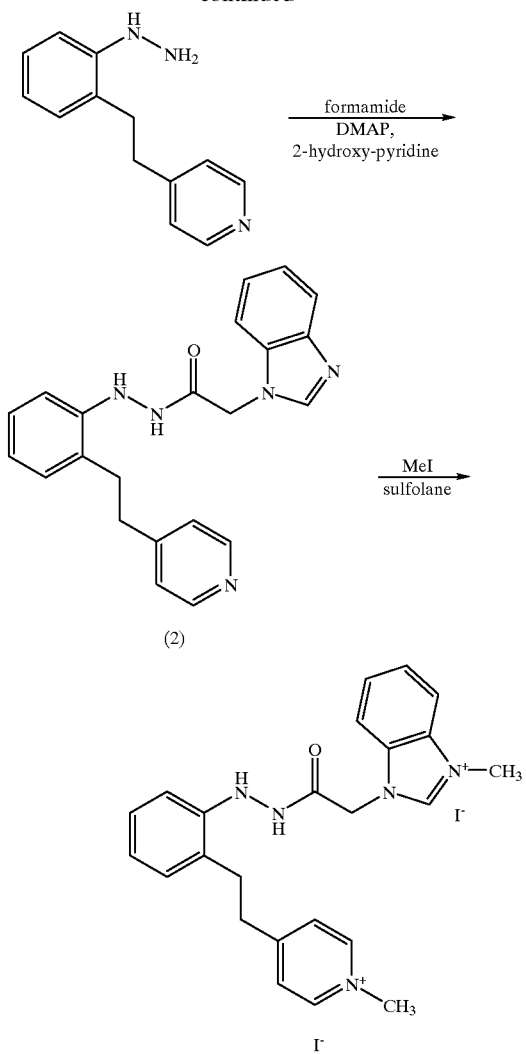

The Synthesis of Compound (2)

0.15 mol of the hydrazine (prepared as describe above, see section I) was dissolved in 50 ml formamide. 0.165 mol of compound (1), 0.015 mol of 4-dimethylaminopyridine and 0.015 mol 2-hydroxypyridine were added and the reaction was allowed to continue for 15 hours at 70° C. After cooling down to room temperature, the mixture was pourred into 400 ml of water. The crude product precipitates from the medium and was isolated by filtration. The crude compound was treated with 300 ml of water, 150 ml of acetone, isolated by filtration and dried. The crude product was recrystallized from proglyde DMM and washed with t.- butyl methyl ether.

The Synthesis of Compound IV 18.8 mmol of compound (2) was dissolved in 35 ml of sulfolane. 56.4 mmol of methyl iodide was added and the reaction was allowed to continue for 2 hours at 42° C. After cooling down to room temperature, the reaction mixture was pourred into 100 ml of ethyl acetate. The solvent was decanted and the oily resdue was treated with 150 ml acetone/ethyl acetate 1/2. On stirring, compound IV crystallized from the medium, was isolated by filtration and washed with ethyl acetate.

Having intensively described the novel class of hydrazide compounds and their preparation we will now describe the photographic material in which these compounds are incorporated as nucleating agents.

The hydrazides used in accordance with the present invention can be incorporated as organic solvent solutions, preferably as methanolic solution.

The nucleating hydrazine compounds of the present invention can be incorporated into the emulsion layer but, alternatively, they can be present in an adjacent hydrophylic layer.

Suitable organic resin supports for use in accordance with the present invention include cellulose nitrate film, cellulose acetate film, poly(vinyl acetal) film, polystyrene film, poly (ethylene terephthalate) film, polycarbonate film, polyvinylchloride film or polyolefin films such as polyethylene or polypropylene film. The thickness of such organic resin film is preferably comprised between 0.025 and 0.25 mm.

In a most preferred embodiment the support is a polyethylene terephthalate support, optionally provided with a subbing layer. An example of a suitable subbing layer is a layer containing a polymer containing covalently bound chlorine. Suitable chlorine containing polymers are e.g. polyvinyl chloride, polyvinylidene chloride, a copolymer of vinylidene chloride, an acrylic ester and itaconic acid, a copolymer of vinyl chloride and vinylidene chloride, a copolymer of vinyl chloride, vinylidene chloride and itaconic acid, a copolymer of vinyl chloride, vinyl acetate and vinyl alcohol, A preferred chlorine containing polymer is co(vinylidenechloride-methylacrylate-itaconic acid; 88%/10%/2%). A most suitable subbing layer contains the latter polymer and a colloidal silica such as KIESELSOL 100F (Bayer AG). Optionally to this composition can be added co(methylacrylate-butadiene-itaconic acid) (49/49/2), preferably in a ratio of about 10%. The most favourable adhesion properties are obtained when a subbing layer as described above provided with an additional primer layer containing gelatin (preferably 0.25–0.35 g/m$^2$), Kieselsol 300 F (0.30–0.40 g/m$^2$) and a matting agent on the base of polymethylmethacrylate (average size 2 a 3 mm) at a coverage of about 0.001 g/m$^2$.

The silver halide emulsion or mixture of emulsions of the photographic material in connection with the present invention can be incorporated in one single layer but, alternatively, a double emulsion layer or even a multiple layer pack can be applied.

The halide composition of the silver halide emulsions used in accordance with the present invention is not specifically limited and may be any composition selected from e.g. silver chloride, silver bromide, silver iodide, silver chlorobromide, silver bromoiodide, and silver chlorobromoiodide. In a prefered embodiment however, the photographic material is a graphic arts material, most preferably, a graphic arts recording material, which by definition is suited for the recording of screened images, linework and/or text, and/or printed circuit board patterns, electronically stored in an image-setter or scanner. Graphic arts recording materials preferably use emulsions containing a majority of chloride, preferably between 50 mole % and 95 mole %, most preferably between 64 mole % and 90 mole %, and a low amount of iodide, the remaining halide being bromide.

The photographic emulsion (s) can be prepared from soluble silver salts and soluble halides according to different methods as described e.g. by P. Glafkides in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). They can be prepared by mixing the halide and silver solutions in partially or fully controlled conditions of temperature, concentrations, sequence of addition, and rates of addition. The silver halide can be precipitated according to the single-jet method, the double-jet method, the conversion method or an alternation of these different methods.

The silver halide particles of the photographic emulsion (s) may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The silver halide grains may have a multilayered grain structure. According to a simple embodiment the grains may comprise a core and a shell, which may have different halide compositions and/or may have undergone different modifications such as the addition of dopes. Besides having a differently composed core and shell the silver halide grains may also comprise different phases inbetween.

Two or more types of silver halide emulsions that have been prepared differently can be mixed for forming a photographic emulsion for use in accordance with the present invention.

The average size of the silver halide grains may range from 0.05 to 1.0 micron, preferably from 0.2 to 0.5 micron. The size distribution of the silver halide particles can be homodisperse or heterodisperse.

The silver halide emulsions can be doped with various metal salts or complexes such as Rhodium and Iridium dopants.

The emulsion can be desalted in the usual ways e.g. by dialysis, by flocculation and re-dispersing, or by ultrafiltration.

The light-sensitive silver halide emulsions are preferably chemically sensitized as described e.g. in the above-mentioned "Chimie et Physique Photographique" by P. Glafkides, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners, gold-selenium ripeners or by means of reductors e.g. tin compounds as described in GB 789,823, amines, hydrazine derivatives, formamidine-sulphinic acids, and silane compounds. Chemical sensitization can also be performed with small amounts of Ir, Rh, Ru, Pb, Cd, Hg, Tl, Pd, Pt, or Au. One of these chemical sensitization methods or a combination thereof can be used.

The light-sensitive silver halide emulsions can be spectrally sensitized with proper dyes such as those described by F. M. Hamer in "The Cyanine Dyes and Related Compounds", 1964, John Wiley & Sons. Dyes that can be used for the purpose of spectral sensitization include cyanine dyes, merocyanine dyes, complex cyanine dyes, complex merocyanine dyes, hemicyanine dyes, styryl dyes and hemioxonol dyes. Particularly valuable dyes are those belonging to the cyanine dyes, merocyanine dyes and complex merocyanine dyes.

The silver halide emulsion(s) for use in accordance with the present invention may comprise compounds preventing the formation of fog or stabilizing the photographic characteristics during the production or storage of photographic elements or during the photographic treatment thereof. Many known compounds can be added as fog-inhibiting agent or stabilizer to the silver halide emulsion. Suitable examples are e.g. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. Other compounds that can be used as fog-inhibiting compounds are metal salts such as e.g. mercury or cadmium salts and the compounds described in Research Disclosure N° 17643 (1978), Chapter VI.

The fog-inhibiting agents or stabilizers can be added to the silver halide emulsion prior to, during, or after the ripening thereof and mixtures of two or more of these compounds can be used.

Besides the silver halide another essential component of a light-sensitive emulsion layer is the binder. The binder is a hydrophilic colloid, preferably gelatin. Gelatin can, however, be replaced in part or integrally by synthetic, semi-synthetic, or natural polymers. Synthetic substitutes for gelatin are e.g. polyvinyl alcohol, poly-N-vinyl pyrrolidone, polyvinyl imidazole, polyvinyl pyrazole, polyacrylamide, polyacrylic acid, and derivatives thereof, in particular copolymers hereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binders of the photographic element, especially when the binder used is gelatin, can be hardened with appropriate hardening agents such as those of the epoxide type, those of the ethylenimine type, those of the vinylsulfone type e.g., 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic material of the present invention may further comprise various kinds of surface-active agents in the photographic emulsion layer or in another hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Other suitable surfactants include perfluorinated compounds. Such surface-active agents can be used for various purposes e.g. as coating aids, as compounds preventing electric charges, as compounds improving slidability, as compounds facilitating dispersive emulsification, as compounds preventing or reducing adhesion, and as compounds improving the photographic characteristics e.g. higher contrast, sensitization, and development acceleration.

Beside the light sensitive emulsion layer(s) the photographic material can contain several non light sensitive layers, e.g. an anti-stress top layer, one or more backing layers, and one or more intermediate layers eventually containing filter- or antihalation dyes that absorb scattering light and thus promote the image sharpness. Suitable light-absorbing dyes are described in i.a. U.S. Pat. Nos. 4,092,168, 4,311,787 and DE 2,453,217. One or more backing layers can be provided at the non-light sensitive side of the support. This layers which can serve as anti-curl layer can contain i.a. matting agents e.g. silica particles, lubricants, antistatic agents, light absorbing dyes, opacifying agents, e.g. titanium oxide and the usual ingredients like hardeners and wetting agents.

The backing layer(s) may further contain an antistatic agent. Suitable antistatic polymers for incorporation in a backing layer are disclosed in e.g. Research Disclosure, April 1990, Item 31237. Further references on ionic conductive polymers include U.S. Pat. Nos. 4,585,730, 4,701,403, 4,589,570, 5,045,441, EP-A-391 402 and EP-A-420 226. An antistatic agent can also be incorporated in a separate layer or in a subbing layer. Relatively recently electrically conducting conjugated polymers have been developed that have electronic conductivity. For ecological reasons the coating of antistatic layers should proceed where possible from aqueous solutions by using as few as possible organic solvents. The production of antistatic coatings from aqueous coating compositions being dispersions of polythiophenes in the presence of polyanions is described in EP 0 440 957.

The photographic elements in connection with the present invention may further comprise various other additives such as e.g. compounds improving the dimensional stability of the photographic element, UV-absorbers, spacing agents and plasticizers.

Suitable additives for improving the dimensional stability of the photographic elements are e.g. dispersions of a water-soluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, α-β-unsaturated dicarboxylic acids, hydroxyalkyl (meth)acrylates, sulphoalkyl (meth)acrylates, and styrene sulphonic acids.

Spacing agents can be present, preferably in the top protective layer. In general the average particle size of such spacing agents is comprised between 0.2 and 10 micron. They can be soluble or insoluble in alkali. Alkali-insoluble spacing agents usually remain permanently in the photographic element, whereas alkali-soluble spacing agents usually are removed therefrom in an alkaline processing bath. Suitable spacing agents can be made e.g. of poly (methylmethacrylate), of copolymers of acrylic acid and methylmethacrylate, and of hydroxypropylmethyl cellulose hexahydrophthalate. Other suitable spacing agents have been described in U.S. Pat. No. 4,614,708.

The photographic materials according to the present invention can, after proper exposure, be processed by any means or any chemicals known in the art depending on their particular application. Preferably however, they are processed in so-called "Rapid Access" chemicals, comprising a conventional Phenidone/hydroquinone or p.-aminophenol/hydroquinone developing solution or an ascorbic acid developing solution, and a conventional sodium- or ammonium thiosulphate containing fixing solution. As explained above their is no need for special "hard dot Rapid Access" developers, although in principle the materials of the present invention can be developed therein. The development time is usually between 10 and 33 seconds at a temperature of about 35° C.

The present invention will now be illustrated by the following examples without however being limited thereto.

EXAMPLES

Example 1

Preparation of the Emulsion

To an aqueous gelatin solution containing sodium chloride, an aqueous solution of silver nitrate and an aqueous halide solution containing potassium bromide, sodium chloride, $2.3 \times 10^{-7}$ mol/mol silver of $Na_3RhCl_6$ and $3.0 \times 10^{-7}$ mol/mol silver of $Na_2IrCl_6$ were added with stirring in accordance with a double jet method to form silver chlorobromide grains having an average grain size of 0.27 μm (variation coefficient: 19%) and a chloride content of 64 mol%.

Thereafter, the emulsion was washed using a conventional flocculation method, and then redispersed with 27 g/mol silver of gelatin. The resulting emulsion was adjusted to pH 5.0 and then chemically sensitized at 50° C. by adding 3.9 mg/mol silver of chloroauric acid and 3.3 mg/mol silver of sodium thiosulfate and digesting for three hours. The emulsion was stabilized with $1.05 \times 10^{-2}$ mol/mol silver of 4-hydroxy-6-methyl-1,3,3a,7-tetraazaindene and $1.4 \times 10^{-5}$ mol/mol silver of 1-p-carboxyphenyl-5-mercaptotetrazole, spectrally sensitized with dye D-1 in an amount of $3.0 \times 10^{-4}$ mol/mol silver.

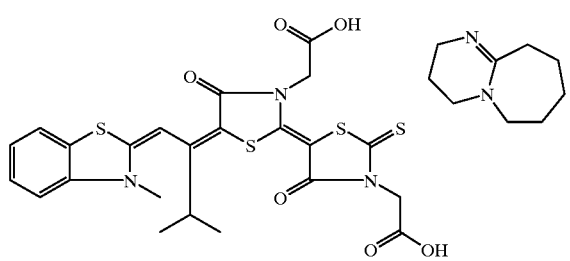
D-1

Preparation of Photographic Samples

The emulsions were coated onto a polyethylene terephthalate film support at 4 g/m$^2$ of silver and were overcoated with a gelatinous anti-abrasion layer containing formaldehyde as hardening agent, 75 mg/m$^2$ of 1-p-carboxy-phenyl-3-pyrazolidone, 216 mg/m$^2$ of hydroquinone, 27 mg/m$^2$ of a fluorine-containing surfactant and 10 mg/m$^2$ of poly (methyl methacrylate) matting agent. The nucleating agents were added as methanolic solutions at the level of $1.0 \times 10^{-3}$ to $3.0 \times 10^{-3}$ mol/mol silver. After the coating the film samples were dried.

Exposure and Photographic Processing

Each sample was exposed to a xenon flash lamp (light emitting time: $10^{-5}$ s.) through both a step wedge and a filter having its peak of transmittance at 622 nm, and then developed for 30 seconds at 35° C. with developer A. Thereafter, it was subjected successively to fixation in a conventional ammonium thiosulphate containing fixation bath, and to washing and drying operations. The processing took place in a Rapiline 66T3 processor (trade mark of Agfa).

Composition of developer A

| | |
|---|---|
| EDTA.Na$_4$ | 2.1 g |
| Hydroxyethyldiphosphonic acid | 0.17 g |
| Potassium carbonate | 39.3 g |
| Potassium sulfite | 45.1 g |
| Potassium bromide | 3.2 g |
| Diethylene glycol | 18.7 ml |
| Hydroquinone | 21 g |
| Sodium erythorbate | 3.2 g |
| 4-Hydroxymethyl-4-methyl-1-phenyl-3-pyrazolidone | 0.367 g |

-continued

| | |
|---|---|
| Methylbenzotriazole | 0.08 g |
| Water to adjust the volume to | 1 l |
| Sodium hydroxide to adjust the pH to | 10.4 |

Evaluation of Image Contrast

Materials with hydrazines typically show in their sensitometric curves a lower gradation at high densities compared to the gradation at low densities. This leads to low image quality and low densities in practical exposures on an imagesetter. Therefore in our evaluation the gradation (γ) was measured between density 3.0+fog and density 3.8+fog. The sensitometric data of the samples are represented in Table 1.

TABLE 1

| Nucleating agent | Concentration (mmole/mole Ag) | Fog | γ | Note |
|---|---|---|---|---|
| Compound I | 2 | 0.03 | 8.8 | Comparison |
| Compound II | 1.5 | 0.03 | 17.9 | Invention |
| Compound IV | 2 | 0.04 | 15.5 | Invention |
| Compound X | 1.5 | 0.04 | 13.3 | Invention |

The samples comprising the new nucleating agents according to the present clearly show an important increase in contrast without a significant increase in fog leading to enhanced image quality for graphic applications.

In a further test the samples were exposed on a red laserdiode image-setter Accuset 1000 (trade mark of Agfa) leading to a 50%-dot pattern after developing in developer A for 30s at 35° C., fixing, washing and drying in a Rapiline 66T3 processor. The dot quality was evaluated with a magnifying glass in order to examine the dots for definition and smoothness. The evaluation is represented by an arbitrary scale. Grade 5 represents a poor, fuzzy, continuous tone type dot. Grade 1 represents an excellent, hard "lith" type dot. The results are summarized in table 2.

The exposed samples were subjected to a running test using a Rapiline 66T3 filled with developer A which was exhausted with 45 m$^2$ fully exposed film during one day. The amount of replenishment was 500 ml per m$^2$. The decrease in density and sensitivity from start to end (expressed as decrease in dot-% at the same exposure) were evaluated and are summarized in table 2.

TABLE 2

| Nucleating agent | Concentr. (mmole/ mole Ag) | Dot quality | Density at exact rendering | Decrease in density | Decrease in sensitivity | Note |
|---|---|---|---|---|---|---|
| Compound I | 2 | 2 | 3.8 | | | Comp |
| Compound I | 3 | 1 | 4.6 | 0.4 | 7 | Comp |
| Compound II | 1.5 | 1 | 5.1 | 0.4 | 2 | Inv |
| Compound IV | 2 | 1 | 5.1 | 0.5 | 0 | Inv |
| Compound V | 2 | 1 | 5.1 | 0.6 | 0 | Inv |

The samples containing the new compounds of this invention clearly show, even at a lower concentration, a significant higher density with the same dot characteristics at exact rendering as compared to the film samples with the comparison nucleating agent. These samples also clearly demonstrate an improvement in stable photographic performances during long run processing.

Example 2
Preparation of the Emulsion

To an acid aqueous gelatine solution containing sodium chloride and potassium bromide an aqueous solution containing silver nitrate and an aqueous solution containing sodium chloride, $1.0 \times 10^{-7}$ mol/mol silver $Na_3RhCl_6$ and potassium bromide were added with stirring in accordance with a double jet method to form silver chlorobromide grains having an average grain size of 0.27 μm (variation coefficient: 23%) and a chloride content of 84%.

Thereafter, the emulsion was washed using a conventional flocculation method, and then redispersed with 27 g gelatin/mol silver. The chemical ripening of the emulsion took place at 57° C. by adding $1.2 \times 10^{-3}$ mol of potassium iodide/mol silver, $1.0 \times 10^{-5}$ mol of chloroauric acid/mol silver, $16 \times 10^{-5}$ mol of sodium sulfite/mol silver, $2.0 \times 10^{-5}$ mol of sodium thiosulfate/mol silver and $1.6 \times 10^{-5}$ mol of sodium p.-toluenethiosulfonic acid with a digestion time of 80 minutes. The emulsion was stabilized with $4.1 \times 10^{-4}$ mol of potassium iodide/mol silver, and $4.7 \times 10^{-4}$ mol of 1-(p-carboxyphenyl), 5-mercaptotetrazole disodium salt/mol of silver.

Preparation of Photographic Samples

The emulsions were coated onto a polyethylene terephthalate (PET) film support at 3.6 g of silver/m² (emulsion layer) and were overcoated with a hydrophilic gelatinous protective layer (overcoat layer).

Emulsion Layer

Emulsion samples prepared as described above were coated from an aqueous solution on a PET support together with the sensitizing dyes D-2 and D-3 in an amount of $1.9 \times 10^{-4}$ mol and $4.3 \times 10^{-4}$ mol per mol of silver respectively.

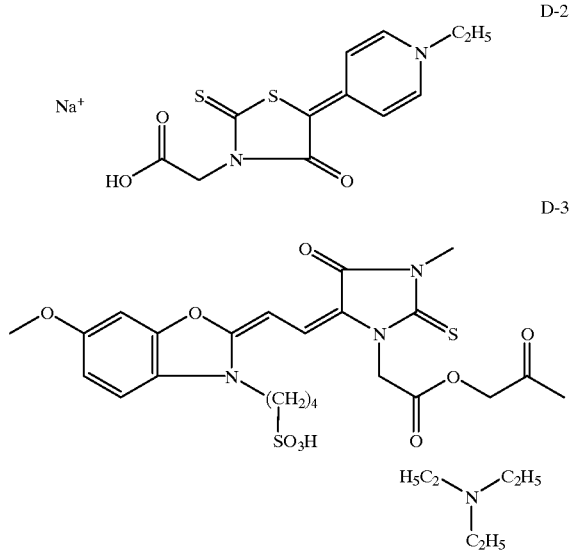

D-2

D-3

The additional stabilizing agents 4-hydroxy-6-methyl-1,3,3a,7-tetraazaindene, 1-(p-carboxyphenyl), 5-mercaptotetrazole disodium salt and phenylmercaptotetrazole were added in an amount of $8.2 \times 10^{-3}$ mol, $7.1 \times 10^{-4}$ mol and $1.1 \times 10^{-4}$ mol per mol silver respectively. For improved physical properties poly(ethylacrylate) and a high molecular weight dextrane were added in a coating amount of 0.4 g and 0.3 g per square meter respectively.

The nucleating agents were added in this layer in amounts of 0.5 to 4 mmol/mol of silver as a solution of water, ethanol or methanol (or mixtures).

Overcoat Layer

Upon the emulsion layer a overcoat layer was coated as a gelatinous anti-abrasian layer containing formaldehyde as hardening agent, 1-p-carboxy-phenyl-3-pyrazolidone (60 mg/m²), hydroquinone (84 mg/m²) as stabilizers, poly(methylmetacrylate) (12 mg/m²) as matting agent and an alkylaryloxypolyoxyethylene carboxylate (27 mg/m²) as surfactant.

The nucleating agents were added in this layer in amounts of 0.5 to 4 mmole/mole of silver as a solution of water, ethanol or methanol (or mixtures). After coating the film samples were dried.

Exposure and Photographic Processing

Each sample was exposed with a Vakuprint™ exposing unit (halogen source) through a continuous tone wedge and a grey filter (D=2) to obtain a continuous tone image for the evaluation of the image contrast.

Each sample was also exposed with a Vakuprint™ exposing (halogen) unit through a step wedge combined with a sinusoidal screen (GNUE-AGST traded by Polychrome) and a grey filter (D=1) to obtain a screened image for the evaluation of the dot sharpness (DS).

The samples were successively processed through an automatic processor Rapiline 66T3 (Agfa) in the upper described developer A (30s, 35° C.), in the 1+4 diluted ammonium thiosulphate containing fixer (30s, 32° C.), washed and dried.

Evaluation of the Sensitometric Properties

The photographic performance of the samples (see table 3) was evaluated by measuring on the samples exposed with the continuous tone wedge the fog level, the speed (S being log H to obtain a density of 3.00 above fog), gamma toe ($\gamma_t$ being gradient between a density of 0.1 and 0.5 above fog), and the gradation (γ defined as gradient between a density of 1.0 and 3.0 above fog). A higher speed is indicated by a lower number. For pepper evaluation the same samples were developed 40s and examination of the pepper was done just before the toe area. The results are represented on an arbitrary scale ranging from 0 (no peppers) to 5 (completely fogged by peppers). A level of 2 is the maximal pepper level that is acceptable.

TABLE 3

| Nucleating agent | concentration (mmole/mole Ag) | Fog | S | $\gamma_t$ | γ | pepper | Note |
|---|---|---|---|---|---|---|---|
| None | — | 0.03 | 2.36 | 2.3 | 8.7 | 0 | comp |
| Compound I | 1.79 | 0.04 | 2.41 | 4.1 | 6.4 | 0.5 | comp |
| Compound I | 3.58 | 0.04 | 2.15 | 7.0 | 8.8 | 1.5 | comp |
| Compound II | 1.12 | 0.04 | 2.25 | 6.3 | 14.1 | 1 | inv |
| Compound II | 1.49 | 0.04 | 2.19 | 7.9 | 20.0 | 0.5 | inv |

TABLE 3-continued

| Nucleating agent | concentration (mmole/mole Ag) | Fog | S | γ$_t$ | γ | pepper | Note |
|---|---|---|---|---|---|---|---|
| Compound II | 1.68 | 0.04 | 2.02 | 7.8 | 20.1 | 0 | inv |
| Compound III | 1.38 | 0.03 | 2.19 | 6.0 | 14.5 | 0.5 | inv |
| Compound IV | 1.28 | 0.03 | 2.26 | 4.5 | 12.1 | 1 | inv |
| Compound X | 1.27 | 0.04 | 2.17 | 5.1 | 24.0 | 0.5 | inv |

It is clear from the table above the samples containing the new compounds in accordance with the invention show clearly a higher speed (lower number being more sensitive), a higher gamma toe and a higher gradation without exhibiting higher fog levels. The new compounds do not generate high pepper levels. This illustrates the definitive higher activity of the invention compounds without loss of selectivity. The remaining low pepper level combined with a lower molar concentration of the nucleating agent are clear advantages.

Evaluation of the Dot Sharpness

The photographic performance of the samples was evaluated by measuring on the samples exposed with a screened image the fog level, the speed (S defined as log H to obtain a density of 1.30 above fog), the screen range (SR being the difference between the speed in log H to reach a density of 0.04 and 1.30 above fog respectively;) and the dot sharpness (DS). The DS is evaluated by using a 50× magnifying glass. The 5%, 50% and 95% dot are examined and evaluated on an arbitrary scale from 0 (best; sharp high dense dot) to 5 (worst; unsharp fuzzy dot of low density). The sum of the three dot quotations (range 0–15) is put in table 4.

TABLE 4

| Nucleating agent | concentration (mmol/mol Ag) | Fog | S | SR | DS | Note |
|---|---|---|---|---|---|---|
| None | — | 0.03 | 2.33 | 1.16 | 12.5 | comp |
| Compound I | 1.79 | 0.03 | 2.30 | 1.09 | 9.5 | comp |
| Compound I | 3.58 | 0.04 | 2.17 | 1.10 | 5.75 | comp |
| Compound II | 1.12 | 0.03 | 2.23 | 1.00 | 5 | inv |
| Compound II | 1.49 | 0.03 | 2.18 | 1.02 | 4.5 | inv |

The table illustrates the big improvement in dot sharpness of the samples containing the invention compounds as compared to the sample without nucleating compound or with the comparison nucleating compound I. Clearly lower concentrations of nucleating agent are needed. No high fog levels or lack in screen range are noticed.

Evaluation of Raw Stock Stability

Non-exposed samples were packaged in a small light-tight cardboard box (=reference) and in a light-tight and humidity-tight folded PAALPO (paper-aluminum-paper laminate) pack. The upper and under samples are not used because they are in direct contact with the PAALPO. The reference box is kept under normal room conditions. The PAALPO pack is kept for five days in a room at 57° C. and 34% RH (relative humidity) as an accelerated ageing test. After that period the samples of the reference and the PAALPO box are at the same time exposed (continuous tone wedge method) and processed in an automatic Rapiline 66T3 processor filled with developer A.

Essential for good raw stock stability is the fact that fog levels must remain low. Fog levels above a density of 0.06 are prohibitive. The results of the upper described samples for shelf life behaviour are shown in table 5.

TABLE 5

| Nucleating agent | concentration (mmole/mole Ag) | DS | Fog ref. | Fog 5d/57 | Note |
|---|---|---|---|---|---|
| None | — | 12.5 | 0.029 | 0.037 | comp |
| Compound I | 1.79 | 9.5 | 0.033 | 0.038 | comp |
| Compound I | 3.58 | 5.75 | 0.030 | 0.083 | comp |
| Compound II | 1.12 | 5 | 0.034 | 0.038 | inv |
| Compound II | 1.49 | 4.5 | 0.038 | 0.041 | inv |

The table clearly shows that when using reference compound I a good dot sharpness (DS) can only be reached with such high levels of nucleating agent that the fog levels after the 5d 57/34 accelerated ageing test are too high. The samples containing the new class of nucleating compounds show a good DS at lower concentration of nucleating agent without giving rise to high fog levels after ageing.

Evaluation of Stability During Exhaustive Processing

The Rapiline 66T3 processor was filled with fresh developor A and subjected to continuous exhaustive processing in a period of one day with 45 m$^2$ of 100% black exposed film with a replenishment rate of 500 ml/m$^2$. This corresponds in practice in a defined replenishment rate of 250 ml/m$^2$ for 50% blackening. Photographic evaluation was performed in the fresh developer and at the end of the test. The difference (0 and 45 m$^2$) in speed and gradation for the continuous tone wedge exposed samples was put in table 6. The difference (end minus start) in speed and dot sharpness for the samples exposed with a screened image was put in table 7.

TABLE 6

| Nucleating agent | concentration (mmole/mole Ag) | S start | S end | γ start | γ end | Note |
|---|---|---|---|---|---|---|
| Compound I | 1.79 | 2.37 | 2.35 | 6.5 | 7.5 | comp |
| Compound I | 3.58 | 2.18 | 2.22 | 8.7 | 8.7 | comp |
| Compound II | 1.12 | 2.32 | 2.29 | 8.1 | 9.0 | inv |
| Compound III | 1.38 | 2.20 | 2.14 | 13.4 | 16.8 | inv |
| Compound IV | 1.28 | 2.31 | 2.26 | 9.7 | 11.6 | inv |
| Compound X | 1.27 | 2.14 | 2.16 | 29.1 | 22.6 | inv |

The table clearly shows that the samples comprising the new compounds retain a much higher gradation during exhaustion than the sample comprising reference compound I in a comparable molar concentration range.

The new nucleating agents do not loose their activity during exhaustion in spite of their lower concentration.

TABLE 7

| Nucleator | concentration (mmole/mole Ag) | S start | S end | DS start | DS end | Note |
|---|---|---|---|---|---|---|
| Compound I | 1.79 | 2.20 | 2.28 | 10.25 | 10.25 | comp |
| Compound I | 3.58 | 2.11 | 2.18 | 5.5 | 6 | comp |

TABLE 7-continued

| Nucleator | concentration (mmole/mole Ag) | S start | S end | DS start | DS end | Note |
|---|---|---|---|---|---|---|
| Compound II | 1.12 | 2.20 | 2.18 | 5.0 | 5.0 | inv |
| Compound II | 1.49 | 2.09 | 2.13 | 5.25 | 5.25 | inv |

The table clearly shows that the samples containing the new nucleating compounds retain a much higher dot sharpness during exhaustion than the sample containing comparison compound I in a comparable molar concentration range.

The new nucleating agents do not loose their activity during exhaustion in spite of their lower concentration. A smaller speed shift for the new compounds is an additional advantage.

What is claimed is:

1. A photographic material comprising a support, at least one emulsion layer, and optionally one or more other hydrophilic layers, characterized in that said emulsion layer or another hydrophilic layer adjacent to said emulsion layer contains a compound according to following general formula I:

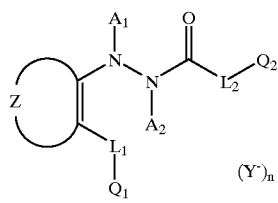

formula I wherein:

1) $L_1$ is a divalent linking group consisting of a linear chain having at most two atoms in said linear chain, 2) $Q_1$ is a cationic nitrogen containing aromatic heterocyclic ring, 3) $L_2$ is a divalent linking group, selected from the group consisting of an alkylene group, an alkylene group having a heteroatom in its chain, an arylene group, a heteroarylene group, and $-CO-N(R)-L_3-$, wherein R represents hydrogen, an alkyl group, an aryl group, or heteroaryl group, and $L_3$ represents an alkylene group, an arylene group, or an heteroarylene group, 4) $Q_2$ is a cationic group, 5) Z represents the necessary atoms to form an aromatic or heteroaromatic ring, 6) each of $A_1$ and $A_2$ independently represents a hydrogen, a group capable of yielding a hydrogen under alkaline photographic processing conditions or a $SO_2R$ group, provided that, if $A_1$ is $SO_2R$, $A_2$ is a hydrogen and vice versa. R represents an alkyl or aryl group, 7) $Y^-$ is a negatively charged counterion to compensate the positive charge of the cationic functional groups.

2. A photographic material according to claim 1 wherein said cationic group $Q_2$ is selected from ammonium, sulfonium and phosphonium.

3. A photographic material according to claim 1 wherein $Q_1$ is a member selected from the group consisting of pyridinium, quinolinium, and isoquinolinium.

4. A photographic material according to claim 1 wherein said divalent linking group $L_1$ is a ethylene group.

5. A photographic material according to claim 1 wherein said photographic material is a graphic arts material.

* * * * *